United States Patent
Phipps et al.

[11] Patent Number: 5,871,460
[45] Date of Patent: Feb. 16, 1999

[54] ELECTROTRANSPORT SYSTEM WITH ION EXCHANGE MATERIAL PROVIDING ENHANCED DRUG DELIVERY

[75] Inventors: J. Bradley Phipps, Maple Grove, Minn.; Lyn C. Moodie, Westbury, N.Y.; J. Richard Gyory, San Jose; Felix Theeuwes, Los Altos Hills, both of Calif.

[73] Assignee: ALZA Corporation, Palo Alto, Calif.

[21] Appl. No.: 418,967

[22] Filed: Apr. 6, 1995

Related U.S. Application Data

[63] Continuation-in-part of Ser. No. 225,470, Apr. 8, 1994, abandoned.

[51] Int. Cl.⁶ .................................................. A61N 1/30
[52] U.S. Cl. ............................................. 604/20; 604/49
[58] Field of Search ........................... 604/20–21, 890.1, 604/49; 607/149, 152, 153, 115; 424/449

[56] References Cited

U.S. PATENT DOCUMENTS

| | | |
|---|---|---|
| 4,585,652 | 4/1986 | Miller et al. . |
| 4,722,726 | 2/1988 | Sanderson et al. . |
| 4,731,049 | 3/1988 | Parsi . |
| 4,744,787 | 5/1988 | Phipps et al. . |
| 4,747,819 | 5/1988 | Phipps et al. . |
| 4,915,685 | 4/1990 | Petelenz et al. . |
| 4,927,408 | 5/1990 | Haak et al. . |
| 5,057,072 | 10/1991 | Phipps . |
| 5,084,006 | 1/1992 | Lew et al. . |
| 5,084,008 | 1/1992 | Phipps . |
| 5,125,894 | 6/1992 | Phipps et al. ........................... 604/20 |
| 5,135,477 | 8/1992 | Untercker et al. . |
| 5,147,297 | 9/1992 | Myers et al. . |
| 5,162,042 | 11/1992 | Gyory et al. ........................... 604/20 |

FOREIGN PATENT DOCUMENTS

| | | |
|---|---|---|
| 410009 | 5/1934 | United Kingdom . |
| 9115260 | 10/1991 | WIPO . |
| 9116943 | 11/1991 | WIPO . |

*Primary Examiner*—Mark Bockelman
*Attorney, Agent, or Firm*—Michael J. Rafa; D. Byron Miller; Steven F. Stone

[57] ABSTRACT

An electrotransport apparatus using dispersed ion exchange material (19,93) is disclosed. The ion exchange material (19,93) may be dispersed in either the donor electrode assembly (10), the counter electrode assembly (10) or both electrode assemblies. The dispersed ion exchange material (93) comprises mobile ionic species (C2) and substantially immobile ionic species (P). The dispersed ion exchange material (93) is consumed during electrotransport of drug or agent (A) in an electrotransport process in which substantially no species which compete with the drug or agent for electrotransport are generated. Electrotransport devices exhibiting reduced polarization are also disclosed.

27 Claims, 1 Drawing Sheet

ELECTROTRANSPORT SYSTEM WITH ION EXCHANGE MATERIAL PROVIDING ENHANCED DRUG DELIVERY

This application is a continuation-in-part of U.S. patent application Ser. No. 08/225,470 filed Apr. 8, 1994, now abandoned.

TECHNICAL FIELD

This invention generally concerns apparatuses for the electrically assisted delivery of therapeutic agent through a body surface such as skin or a mucosal membrane. Such apparatuses are referred to broadly herein as electrotransport devices.

More specifically, this invention relates to electrotransport drug delivery devices or systems in which active species, agents or drugs are directly or indirectly delivered through a body surface (eg, skin) of a patient by application of electromotive force.

BACKGROUND OF THE INVENTION

The present invention concerns apparatuses for transdermal delivery or transport of therapeutic agents, typically through iontophoresis. Herein the terms "electrotransport", "iontophoresis", and "iontophoretic" are used to refer to methods and apparatus for transdermal delivery of therapeutic agents, whether charged or uncharged, by means of an applied electromotive force to an agent-containing reservoir. The particular therapeutic agent to be delivered may be completely charged (ie, 100% ionized), completely uncharged, or partly charged and partly uncharged. The therapeutic agent or species may be delivered by electromigration, electroosmosis or a combination of the two. Electroosmosis has also been referred to as electrohydrokinesis, electro-convection, and electrically-induced osmosis. In general, electroosmosis of a therapeutic species into a tissue results from the migration of solvent, in which the species is contained, as a result of the application of electromotive force to the therapeutic species reservoir, ie, solvent flow induced by electromigration of other ionic species. Thus, as used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

During the electrotransport process certain modifications or alterations of the skin may occur such as increased ionic content, hydration, dielectric breakdown, extraction of endogenous substances and electroporation. Any electrically assisted transport of species enhanced by modifications or alterations to a body surface (eg, formation of pores in the skin) are also included in the term electrotransport as used herein.

Iontophoretic devices for delivering ionized drugs through the skin have been known since the 1800's. Deutsch United Kingdom Patent No. 410,009 (1934) describes an iontophoretic device which overcame one of the disadvantages of such early devices, namely, that the patient needed to be immobilized near a source of electric current. The Deutsch device was powered by a galvanic cell formed from the electrodes and the material containing the drug to be transdermally delivered. The galvanic cell produced the current necessary for iontophoretically delivering the drug. This device allowed the patient to move around during iontophoretic drug delivery and thus required substantially less interference with the patient's daily activities.

In present iontophoresis devices, at least two electrodes are used. Both of these electrodes are disposed so as to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, eg, a battery; and usually to circuitry capable of controlling current passing through the device. For example, if the ionic substance to be driven into the body is positively charged, then the positive electrode (the anode) will be the active electrode and the negative electrode (the cathode) will serve to complete the circuit. If the ionic substance to be delivered is negatively charged, then the cathodic electrode will be the active electrode and the anodic electrode will be the counter electrode.

Furthermore, existing iontophoresis devices generally require a reservoir or source of the beneficial agent or drug, preferably an ionized or ionizable species (or a precursor of such species) which is to be iontophoretically delivered or introduced into the body. Such drug reservoirs are connected to the anode or the cathode of an iontophoresis device to provide a fixed or renewable source of one or more desired species or agents.

Perhaps the most common use of iontophoresis today is in diagnosing cystic fibrosis by delivering pilocarpine transdermally. Iontophoretically delivered pilocarpine stimulates sweat production, the sweat is collected, and is analyzed for its chloride ion content. Chloride ion concentration in excess of certain limits suggests the possible presence of the disease.

Thus an electrotransport device or system, with its donor and counter electrodes, may be thought of as an electrochemical cell having two electrodes, each electrode having an associated half cell reaction, between which electrical current flows. Electrical current flowing though the electronically conductive (eg, metal) portions of the circuit is carried by electrons (electronic conduction), while current flowing through the liquid-containing portions of the device (ie, the drug reservoir in the donor electrode, the electrolyte reservoir in the counter electrode, and the patient's body) is carried by ions (ionic conduction). Current is transferred from the metal portions to the liquid phase by means of oxidation and reduction charge transfer reactions which typically occur at the interface between the metal portion (eg, a metal electrode) and the liquid phase (eg, the drug solution). A detailed description of the electrochemical oxidation and reduction charge transfer reactions of the type involved in electrically assisted drug transport can be found in electrochemistry texts such as J. S. Newman, *Electrochemical Systems* (Prentice Hall, 1973) and A. J. Bard and L. R. Faulkner, *Electrochemical Methods, Fundamentals and Applications* (John Wiley & Sons, 1980).

As electrical current flows, oxidation and reduction of a chemical species takes place. A variety of electrochemical reactions can be utilized, and these generally fall into two major classes. In one major class, the electrochemical reaction results in the generation of a mobile ionic species with a charge state (ie, + or −) like that of the drug in its ionic form. Such a mobile ionic species is referred to as a "competitive species" or a "competitive ion" because the species competes with the drug for delivery by electrotransport. Exemplifying this class of reactions is what is referred to in the art as a "sacrificial" reaction where electrode material is consumed in the reaction with generation of a competitive ion. A further example of this first major class of electrochemical reactions is a de-intercalation reaction where a competitive ion is expelled from the electrode. A third example of this first major class of electrodes is the common situation where a competitive ion is generated by oxidation or reduction of a substance in contact with the electrode. Reactions falling in the first major class may be either anodic or cathodic.

Examples of anodic reactions where a competitive cation is generated include:

$$M^0 \rightarrow M^{Z+} + Ze^- \quad (1)$$

where $M^0$ is a metal which is oxidized to the +Z state and $M^{Z+}$ is the competitive ion;

$$M_xWO_3 \rightarrow M_{x-1}WO_3 + M^+ + e^- \quad (2)$$

where $M^+$ is the competitive ion, and $$H_2Q \rightarrow Q^0 + 2H^+ + 2e^- \quad (3)$$

where $Q^0$ is a species which is stable in its reduced state and $H^+$ is the competitive ion.

Examples of cathodic reactions where a competitive anion is generated include:

$$AgCl + e^- \rightarrow Ag^0 + Cl^-. \quad (4)$$

$$C_nFeCl_3 + e^- \rightarrow C_nFeCl_2 + Cl^- \quad (b\ 5)$$

and $$Cl_2 + 2e^- \rightarrow 2Cl^- \quad (6)$$

where $Cl^-$ is the competitive anionic species in each of reactions, 4, 5, and 6.

In a second major class of electrochemical reactions, no competitive ion is generated during the operation of the system. In one example of this class of reactions, the species to be reduced or oxidized exist in solution and the charge transfer oxidation or reduction reaction is catalyzed at the electrode surface. The products of the reaction are gaseous or soluble in the reservoir and either are neutral or exist in a charge state opposite that of the drug in its ionic form. A reaction product having a charge state opposite that of the drug to be delivered would not be "competitive" as the term is used here. Examples of anodic reactions of this latter class which do not generate a competitive ion include:

$$Fe(CN)_6^{4-} \rightarrow Fe(CN)_6^{3-} + e^- \quad (7)$$

$$C_nFeCl_2 + Cl^- \rightarrow C_nFeCl_3 + e^-. \quad (8)$$

Examples of cathodic reactions which do not generate a competitive ion include:

$$M^{Z+} + ze^- \rightarrow M^0 \quad (9)$$

$$M_{x-1}WO_3 + M^+ + e^- \rightarrow M_xWO_3 \quad (10)$$

$$Q^0 + 2H^+ + 2e^- \rightarrow H_2Q, \quad (11)$$

and $$Fe^{3+} + e^- \rightarrow Fe^{2+}. \quad (12)$$

Reactions 7, 9, 11, and 12 are catalyzed by an appropriately polarized surface of a substantially inert or catalytic electrode, such as the surface of a catalytic electrode comprising carbon, gold, stainless steel or platinum. Reactions 8 and 10 are intercalation/insertion reactions where an ionic species is incorporated into the electrode material during operation of the device.

It is particularly important in attempting to determine which of the above major classes a particular system falls into, to focus upon the species generated during the electrochemical reaction(s) as it (or they) relate to the drug or agent to be delivered. In particular, the focus should be whether the species generated will electromigrate in the same direction (eg, toward the skin) as the drug or agent of choice under the influence of the electric potential gradient. In other words, it is significant that an ionic species is being produced only in so far as ionic species competes with a drug or agent to be delivered and thereby adversely impacts biocompatability of the electrotransport system (eg, where the competing ionic species produced is not biocompatible), drug stability, or drug delivery efficiency.

In the prior art, iontophoresis electrodes employing the first approach, above, have usually included current distributing members or structures referred to as "active" or "electroactive" or "electrochemically reactive" in the sense that their chemical compositions were materially altered during the agent delivery process. For example, sacrificial current distributing members which were oxidized or reduced themselves have been discussed. Use of sacrificial current distribution members can avoid the adverse effects associated with utilization of catalytic current distributing members (eg, pH changes). Electrodes with sacrificial current distributing members are disclosed in U.S. Pat. No. 4,744,787 to Phipps, et al and U.S. Pat. No. 5,135,477 to Untereker, et al. Intercalation electrodes are discussed in patents issued to those same inventors.

The current distributing member in an iontophoresis electrode employing the second approach, above, have usually been constructed to include substantially inert materials such as stainless steel or platinum. "Inert" as that term is used in the art normally means that the material is catalytic, ie, it catalyzes an oxidation or reduction reaction by providing or accepting electrons to or from other chemical species but does not itself take part in the reaction by being chemically or physically altered. The material of the electrode structure, eg, the current distributing member, therefore is "inert" only in the sense of itself not being chemically altered in the reduction or oxidation reaction in which it participates.

When oxidation or reduction occurs at an electrode surface, ionic species must be transported to maintain electroneutrality throughout the system. Electrically-assisted transport or electrotransport is defined as the mass transport of a particular chemical species through a biological interface or membrane when an electrical potential gradient is imposed across said interface or membrane. Four physical processes contribute to this transport: passive diffusion, electromigration, electroporation, and convection. Even though drug electrotransport systems are well characterized, there is a continuing need to enhance their drug delivery efficiency. Enhanced efficiency permits smaller, less expensive and more versatile devices to be developed. Optimization of the three physical transport processes is one approach to enhance such efficiency.

In the iontophoresis art, various approaches have been taken to increase the drug delivery efficiency of (ie, the amount of drug delivered per unit of applied electrical current) transdermal drug or agent delivery. This issue was addressed in U.S. Pat. No. 5,135,477 to Untereker et al and in earlier related U.S. Pat. Nos. 4,744,787 and 4,747,819 both to Phipps et al. The above patents disclose increased electrotransport drug delivery efficiency by the selection, (in accordance with the Untereker et al patent) of: (1) the particular form of the drug to be delivered, (2) an electrochemically active component of the drug delivery apparatus, or (3) both, so that during the operation of the apparatus competitive species (i.e, ions carrying the same charge as the drug ions and thus in competition with the drug for carrying current into the body) were reduced or eliminated. The basic solution proposed by Untereker et al has the drawback in that the particular agent or drug to be iontophoretically delivered may be unavailable in a form with the desired counter ion. Even if the drug is available in the proper salt form (eg, when using a silver anodic electrode, the drug is preferably in the form of a chloride salt so that the drug counter ion is chloride), the net or overall electrochemical process ($Ag+Cl^- \rightarrow AgCl+e^-$) may require more counter ion (eg, $Cl^-$) than can be supplied by the drug salt alone. This is particularly true for highly potent or expensive drugs, where the concentration of drug salt within the reservoir is generally relatively small. Put otherwise, a particular combination of drug/drug counter ion, and electroactive component of the device to enhance efficiency of the device in accordance with the teachings of the above patents may not be practical due to limitations on the availability of drug salt in the appropriate form or the amount of drug salt that can be added to the reservoir. It is one objective of this invention to overcome these limitations by providing electrochemically appropriate ions from a source other than, or in addition to, those supplied by the drug salt so as to enhance agent or drug delivery efficiency.

Subsequent to the work of Untereker et al noted above, several patents have disclosed the use of various means to inhibit the flow of ions competitive with the species to be delivered. U.S. Pat. No. 4,722,726 to Sanderson et al discloses an iontophoresis device having an ion mobility inhibiting means (ie, a discrete layer of ion exchange membrane material) disposed between, for example, an electrode/electrolyte solution and a source of the ionic species to be delivered, ie, a drug solution. The ion exchange membranes used by Sanderson et al included the AR103-QZL membrane sold by Ionics, Inc. and Raipore 4010 and 4035 membrane sold by RAI Research Corp. A device of the Sanderson et al patent has electrodes which generate hydronium ions and hydroxyl ions during its operation. Thus, the purpose of Sanderson's ion-exchange membrane is to inhibit the passage of ions of similar charge (ie, similar to that of the drug ion) from the electrode/electrolyte solution to the drug solution where they could compete. However, Sanderson et al do not attribute any significance to the selection of the ion exchange medium counter ion. Of particular significance is the fact that the ion exchange membrane disclosed by Sanderson et al is selectively permeable to ions having a charge which is opposite the charge of the drug species to be delivered. To function properly, the ion exchange material must provide a continuous barrier to the passage of ions carrying the same charge as the drug ion.

U.S. Pat. No. 4,731,049 to Parsi discloses an iontophoresis device employing a drug reservoir in which the drug to be delivered is initially bound to an ion exchange medium or an immobilized ligand affinity medium. Ions such as hydrogen ($H^+$), sodium, potassium, hydroxyl, chloride, and sulfate ions are generated at the electrode or provided by an ion reservoir and are exchanged for the bound drug ions, thereby releasing the drug ions for delivery into the patient's body. Parsi discloses a donor electrode assembly having a hydrophilic polymer-based electrolyte reservoir and drug reservoir layers, a skin-contacting hydrogel layer, and optionally one or more semipermeable membrane layers. The ion exchange media is disclosed to be in the form of beads, powder, packed fibers, woven or knit fibers, microporous or macromolecular resin or liquid resin. Parsi employs electrodes which are electrochemically catalytic, ie, the electrodes are composed of materials (eg, carbon, graphite or metal, such as platinum group metals) which catalyze the electrochemical reaction as described above. Parsi is limited in its application to systems where drug can be bound to an ion exchange resin or medium or an immobilized ligand affinity medium, and for this reason, must possess a charge opposite that of the drug ion. U.S. Pat. No. 4,915,685 to Petelenz et al discloses a system closely related to that disclosed by Parsi.

U.S. Pat. No. 4,927,408 to Haak et al discloses an electrotransport system having a novel donor electrode pad. The pad comprises an agent reservoir, and an electrolyte reservoir separated by a selectively permeable membrane. Microporous polymers, ie, membranes, which are selectively permeable based on the size of the permeating species and ion-exchange membranes which are selectively permeable based on the charge of the permeating species, are disclosed to be useable in the electrode pad of Haak. The charge selective membranes of Haak can be selected to bind, eg, by ion-exchange or chelation, particularly interfering or undesirable species. For example, interfering metals can be removed by this expedient.

Related to the above Haak et al '408 patent is International Application No. WO91/16943 which provides substantial additional detail regarding selectively permeable membranes which are selective for the particular size or molecular weight of the diffusing species.

European Patent Application WO91/15260 (PCT/US91/02030) discloses, in one embodiment, an iontophoretic device having a two layer active electrode element. A single layer active electrode element embodiment also is disclosed. In the embodiments disclosed in the '15260 application, layers of anionic, cationic or amphoteric polymers are used. In a preferred structure, an impermeable layer is interposed between the two layers of the electrode. Enhancement of shelf life is a particular objective of the '15260 application.

U.S. Pat. No. 4,585,652 to Miller et al discloses delivery of bioactive substances using an electrode comprising a polymer which is "charged" or conductive and which can be electrochemically cycled between a charged and a neutral or insulating state. In the charged state, the polymer is located with bioactive counter ions which are delivered when the polymer is cycled to the neutral state. An example of a charged polymer is poly(vinylferrocene). Examples of conductive polymers are poly(pyrroles), substituted poly (thiophenes), and similar poly(heterocyclic) materials.

U.S. Pat. No. 5,057,072 to J. B. Phipps discloses an iontophoresis electrode which uses a current distribution member and a drug reservoir containing an ionic drug. The current distribution member is separated from the drug reservoir by a membrane or a material selective for ions having a charge opposite to the charge of the drug to be delivered. The cation or anion selective layer or coating of material is applied directly to the current distributing member and prevents the migration into the drug reservoir of ions produced during the oxidation or reduction of the current distributing member.

U.S. Pat. No. 5,084,008 to J. B. Phipps discloses an improved iontophoresis electrode having a current distribution member in direct or intimate contact with a salt layer or an ion source layer. In direct or intimate contact with the salt layer or ion source layer is a size selective membrane (ie, a semipermeable membrane) or a material which is charge selective for ions having a charge opposite to the charge of the drug to be delivered. This improved structure of the iontophoresis electrode is preferably employed using a current distributing member which is itself oxidized or reduced during the process of drug delivery.

The above patents which disclose the utilization of charge selective layers or membranes to enhance device efficiency operate on the theory of Donnan exclusion. Donnan exclusion, in the case of a charge selective membrane (eg, an ion-exchange membrane), means that the fixed charge of the membrane reduces the likelihood that ions or molecules having a similar charge from passing through the membrane due to electrostatic repulsion. The type of fixed charge, and the charge density within the ion pathways favor the passage of species having definable characteristics, ie, a charge which is opposite the fixed charge on the membrane. Utilization of the principle of Donnan exclusion, in the context of an electrotransport device having a charge selective membrane, has the drawback of tending to create polarization within the entire device or within a device component. An increase in polarization tends to increase the voltage necessary to deliver agent or ion. A voltage increase within an electrotransport device normally requires an increase in the number of batteries to operate the device and therefore an increase in device size, device complexity, device cost or a combination of these factors.

Size exclusion, in the case of a size selective membrane, means simply that the pore size of the membrane is too small to permit specific molecules or ions to pass. Physical size or molecular weight restriction prevents or hinders the passage of species through the membrane. Utilization of size selective membranes also can create polarization as discussed above if the "excluded" species tend to have the same (+/−) charge.

The present invention overcomes the problems encountered in the prior art and is not suggested or disclosed in the references alone or in combination. Moreover, utilization of the present invention tends to permit smaller, less complex and less expensive electrotransport devices to be built. In addition, the present invention allows utilization of a wider variety of salts and lower drug content than is possible with prior art devices.

DISCLOSURE OF THE INVENTION

The present invention derives from the discovery that a discrete layer, membrane, ion mobility inhibiting means or zone is not necessary to the enhancement of electrotransport drug or agent delivery. In particular, this invention relates to the incorporation of ion exchange materials which, in one aspect, provide a means of rendering competitive ions substantially immobile, and in another aspect provide a means of facilitating an electrochemical reaction where no competitive species are generated.

In one aspect, the present invention is an electrode assembly for an electrotransport delivery device comprising an electrode and at least one distributed or dispersed ion exchange material. An ion exchange material of this invention comprises mobile ionic species and substantially immobile ionic species. In one practice, the ion exchange material or ion exchange macromolecule is uniformly or homogeneously dispersed in the drug reservoir. In a less preferred practice, the ion exchange material is uniformly dispersed within an "in-line" skin contact adhesive, which adhesive is placed between the drug or salt (counter) reservoir and the patient's skin and which helps secure the reservoir to the patient. In a more preferred practice, the electrode, itself, will be a composite structure comprising an electronically conductive composition and an ion exchange material.

The mobile ionic species chosen will be of a type which interacts with a competitive species generated during operation of the electrotransport device so as to render the competitive species substantially immobile or otherwise making it substantially non-responsive to external electromotive forces. A suitable ion exchange material is generally substantially insoluble in the medium in which it is dispersed. Generally, this means the ion exchange material will be substantially insoluble in (1) the liquid solvent used to "hydrate" the reservoir matrix (most typically, the reservoir matrix is hydrated with water due to its excellent biocompatibility) and (2) the polymer of the electrode or reservoir matrix. More preferably, the ion exchange material has a minimal water soluble fraction since any low molecular weight water soluble fraction has the potential to be undesirably delivered into the patient by electrotransport. The water soluble fraction of any ion exchange material can be determined by washing the resin in water and calculating the weight loss of the material. Preferably, the ion exchange material has a water soluble fraction of less than about 0.1 wt % and most preferably less than about 0.001 wt %. The ion exchange material, while dispersed within a reservoir, may be in direct and intimate contact with an electrode or current distributing member. The ion exchange material described herein may be located essentially anywhere within ion conducting portions of the electrotransport device, provided most or all competitive ionic species generated during operation of the device interact with the mobile ionic species of the ion exchange material before they reach the skin surface of the agent recipient and thereby become immobilized. While the ion exchange material may be dispersed within any ion-conducting portion or portions of the electrotransport device, it is preferred to place the dispersed ion exchange material as far away from the patient body surface-contacting portions of the device as is possible. Thus, the ion exchange material is least preferably dispersed in a layer of skin-contacting adhesive positioned between the drug reservoir and the skin, is more preferably dispersed in the drug reservoir, and is most preferably dispersed in the current distribution elements (ie, the electrodes) of the device.

When a sacrificial electrode is chosen to deliver a positively charged drug ion, $D^+$, (and assuming all other factors such as concentration are equal), the competitive ions generated at the anode in the oxidative process, will be positively charged metal ions. The ion exchange material is chosen in view of the competitive ion(s) generated with the express intent of rendering the positively charged competitive ion(s) immobile or at least substantially non-responsive to electromotive forces or electromigration tendencies. Thus an electrode assembly of this invention, by inclusion of a dispersed ion exchange material, will effectively reduce iontophoretic delivery of oxidatively produced ions which compete with the drug or agent to be delivered. This increases the efficiency associated with delivery of the drug or other beneficial agent. It is a further advantage of this invention that the cations generated during operation of the device, particularly metal cations, may have an undesirable toxicity. Prevention of such toxic species from reaching the skin, and the attendant reduction in possible toxicity due, eg, to the presence of metal cations, is a particular advantage of this invention. A further advantage of this invention is the reduction of the drug degradation processes which metal cations sometimes cause.

In a further practice of this invention, the above ion exchange material or materials are selected to provide some other desired property to the electrode structure or component in which it is dispersed. For example, the ion exchange material may provide hydrophilicity or other desirable property to the assembly component in which it is dispersed.

In yet another practice of this invention, the ion exchange material may be uniformly dispersed or distributed throughout each of several individual ion conducting portions of the electrode assembly. This approach tends to reduce the overall electrode thickness, to reduce polarization, and enhance drug or agent delivery efficiency of this device.

The terms "immobile" or "immobilized" are used extensively herein. Those terms are to be broadly construed to mean any of the physicochemical processes or interactions which produce or generate a species which does not compete with the drug ion (or which can migrate only to a limited extent), because of size or charge state in response to an electromotive force. Specifically, and without limitation, the physicochemical processes or "interactions" intended by this terminology include deposition, precipitation, neutralization, intercalation, association, complexation or chelation. The net effect of the interaction, "capture", or "binding" process is to render the competitive species substantially immobile. This interaction can occur within or in the vicinity of the ion exchange material or the ion exchange material may provide a source of mobile species which interact with the competitive species outside or far from the ion exchange material, as long as the competitive species generated is essentially prevented from migrating into the body surface. While irreversible interactions are preferred, reversible interactions may also be adequate provided that the mobility or concentrations of the reversibly-held, unwanted, competitive species is reduced substantially below the mobility or concentration of the agent to be delivered. Preferably, the transport number of the competitive species is less than 50%, more preferably less than 1%, of the transport number of the active agent being delivered when the device of the present invention is in operation.

The term "ion exchange material" is used extensively herein. This term is also to be broadly construed to mean essentially any material comprising mobile ionic species and substantially immobile ionic species where the immobile ionic species has the same charge state as the drug or agent but has sufficient mass, size, or molecular weight so as to reduce substantially its mobility in response to an applied electromotive force. It is to be understood, however, that most species will have at least some mobility in response to electromotive forces. Other terms used to describe the immobile ionic species which comprises a part of the ion exchange material include polymer, copolymer, oligomer, ionomer, polyelectrolyte, resin, colloid, micelle, particle and the like. An ion exchange material of this invention may be synthetic or natural.

While the ion exchange material used herein will generally be primarily organic in composition (ie, hydrocarbon-based) it is within the contemplation of this invention that the ion exchange material may be primarily inorganic in composition (eg, a ceramic composition). Generally speaking, the immobile ionic species will have a number average molecular weight in the range of at least about ten times greater than the molecular weight of the drug or agent to be delivered by electrotransport. A preferred polymeric immobile ionic species would be crosslinked and thereby rendered substantially insoluble in water.

Much of the above discussion relates to the class of electrochemical reactions where competitive ionic species are generated. As is noted above, there is a second class of reactions where no competitive ionic species are generated. In this later class of reactions, the dispersed ion exchange material will provide at least one of the reactants. By providing reactant (in part or in their entirety) the ion exchange material enhances the likelihood of occurrence of the reaction (or reactions) where no competitive ions are generated. Illustrating this, to facilitate electrotransport of an anionic drug $D^-$, the ion exchange material would provide a mobile cation which is reduced at the cathode as is suggested by reactions 9 and 12, above. These reduction reactions would be catalyzed at the surface of the cathode.

In the case where the cathode is an intercalation material (eg, $M_{x-1}WO_3$ or conductive polymers like those suggested by Miller et al U.S. Pat. No. 4,585,652), then the ion exchange material would provide ionic species capable of participating in the intercalation reaction. For example, if the cathode were sodium tungstate in a partially oxidized state, then the ion exchange material would provide a source of sodium ion or other cation capable of being intercalated into the cathode structure during operation of the device, as indicated by reaction 10 above.

As a third example, the ion exchange material may provide an ionic species, opposite in charge state to the drug in its ionic form, which is not reduced at the cathode nor intercalated into the cathode, but instead is a reactant critical to the formation of a noncompetitive product. This type of scenario is suggested by reaction 11 above. In this case, the ion exchange material is a source of hydronium ion, $H_3O^+$. Ion exchange materials with mobile hydronium ions have been employed in the prior art as buffering agents (eg, Sanderson U.S. Pat. No. 4,722,726 to counteract the effect on reservoir pH due to generation of hydroxyl ion at the cathode (eg, via the reaction $H_2O+e^- \rightarrow \frac{1}{2}H_2+OH^-$). In contrast, this example of the invention utilizes an ion exchange material as a source of hydronium ion which facilitates the formation of a noncompetitive species (eg, $H_3O^+ + OH^- \rightarrow 2H_2O$).

The above examples of this invention have focused on anodic and cathodic reactions. Anodic reactions were selected to illustrate the use of ion exchange materials for the "capture" of competitive ions generated at the anode. Cathodic reactions were used to illustrate the use of ion exchange materials for the "facilitation" of reactions, which generate no competitive ions. This was done to simplify the discussion and is not intended to restrict the use of ion exchange materials for one purpose or the other to a particular type of electrode, ie, anode or cathode. Ion exchange materials can be used for either purpose at either electrode, as appropriate for the particular drug to be delivered. In addition, the principles illustrated above can be used in conjunction with the counter electrode of the device to prevent generation or delivery of toxic or otherwise "unwanted" species into or out of the counter electrode reservoir whether or not such species are "competitive" as the term is used herein.

A "composite electrode structure", "composite drug reservoir", "composite electrode" or "composite material" as those terms are used herein mean that the reservoir, electrode, material or structure comprises at least two physically or chemically distinct phases. The ion exchange material comprises one phase which would be dispersed within one or more other materials or phases. Because the ion exchange material is dispersed within the composite structure in accordance with this invention (ie, there is no discrete layer, membrane or highly-concentrated zone of ion exchange material), ion migration is not required to occur through the ion exchange material. In a preferred practice, the ion exchange material is commingled with the electroactive substance thereby generating a composite electrode structure, or less preferably is commingled with the drug substance within the drug reservoir thereby generating a "composite" drug reservoir structure.

Put another way, an ion exchange material of this invention is not present as a discrete or continuous structure (eg, a membrane or layer), which separates one component of the device from another. Instead, the ion exchange material is distributed, within and throughout the electrode, the drug reservoir, the skin adhesive or other structure (or each structure) of the electrotransport system. Generally speaking, dispersed ion exchange materials are particulate, having a major dimension in the range of about 0.1 to 1200 microns. Particle sizes at the lower end of this range, eg, about 1 to 600 microns and most preferably in the range of about 5 to 150 microns, are preferred from the standpoint of case of processing and manufacturability. The ion exchange material, to be effective, must be in a drug or agent-transmitting relationship in the system. This means the material, regardless of where it is located, must be able to interact with the drug or agent flux during electrotransport.

The term "distributed" as used herein is not necessarily intended to mean "uniformly distributed", within the device structure. The term "distributed" means that the ion exchange material is sufficiently dispersed, whether particles, grains, pellets, colloids, or micelles, so that ionic polarization due to size selectivity or charge selectivity within the operant portion of the device, is substantially avoided.

DETAILED DESCRIPTION OF THE INVENTION

Figure 1:
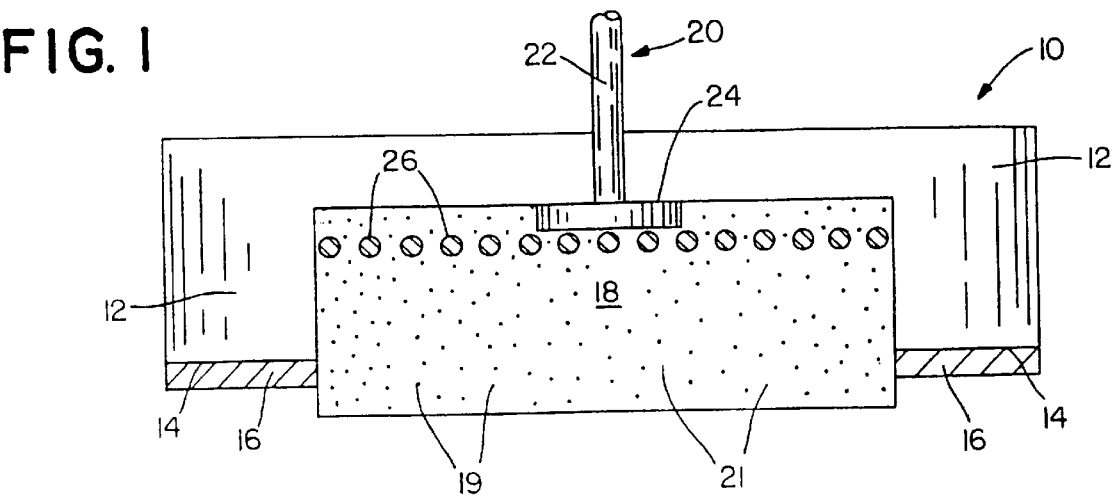
FIG. 1 is a cross-sectional view of an electrotransport electrode according to the present invention.

Reference is now made to FIG. 1 included herewith. In the FIG. 1, there is depicted, schematically, in cross section, a single, substantially circular donor electrode assembly 10 which is intended for use in an iontophoretic drug delivery device. It is to be understood that electrode assembly 10 is but one of the two electrode assemblies necessary for operation of a device and that a necessary source of electrical energy, eg, a battery, also is not shown.

Electrode assembly 10 comprises an insulative support or housing which, in cross section, is generally "U" shaped and which preferably is flexible. In a preferred embodiment, support 12 is produced from a self-supporting, non-conductive polymeric foam. In this embodiment, perimeter surface 14 of housing 12 optionally has disposed thereon a skin-compatible, pressure-sensitive biomedical adhesive 16 which holds electrode assembly 10 in place on the patient's skin during iontophoretic drug delivery. Electrode assembly 10 may be held in place by other means, eg, a strap (not shown), or in certain cases matrix 21 (discussed below) is itself sufficiently adhesive to adhere electrode assembly 10 to the skin, in which instances adhesive 16 would not be needed. In the instance where matrix 21 is sufficiently adhesive, ion exchange material could be dispersed within matrix 21. Under these circumstances, the ion exchange material would be in a drug or agent transmitting relationship with respect to a patent, as that term is used herein. In this embodiment, a periphery adhesive could be omitted or redundant.

Electrode assembly 10 includes an electroactive electrode 20. Electrode 20 includes an exterior connector wire 22, a current distribution member which includes a tab or plate 24 and an optional screen 26. The screen is included only to ensure good contact between the gel matrix 21 and the current distribution member. In one embodiment, electrode 20 would be comprised of silver.

Electrode 20 may have other structures. For example, the electrode described in U.S. Pat. No. 5,147,297 at column 3, lines 44–60, which description is incorporated by reference herein, may be utilized in a practice of this invention. Moreover, as used herein the term "electrode" is not intended to require, but may include, associated drug or electrolyte reservoirs.

Also shown in FIG. 1 is a drug reservoir 18 which, in one practice, comprises a gel or a gel matrix 21. Gel matrix 21 contains the drug or agent species (not shown) which is to be transdermally delivered across the skin barrier. The drug is uniformly dispersed in matrix 21. Drug concentrations in the range of $1 \times 10^{-4}$M to 1.0M or more can be employed, with drug concentrations in the lower portion of this range being preferred. (A gel matrix such as that described with respect to the drug reservoir of the donor electrode assembly can be utilized in the electrolyte reservoir associated with the counter electrode assembly.)

Any of a number of possible gel matrices may be employed. Agar, polyvinylalchohol, or polyvinylpyrrolidone gels, and the like are well known to one skilled in this art and are advantageously used. If some sort of barrier is employed to define the lower perimeter of reservoir 18, then a non-self supporting, lower-viscosity material may be used. A preferred reservoir material usable for either agent or electrolyte is described in U.S. Pat. No. 5,084,006, which patent is incorporated by reference herein. The reservoir material described in the '006 patent comprises about 10 to 60 weight percent hydrophilic polymer, about 10 to 60 wt. % of a hydrophobic polymer and up to about 50 wt. % of agent or about 60 wt. % electrolyte.

In operation, electrode assembly 10 is placed in contact with a patient's skin and pressed with sufficient firmness so that pressure sensitive adhesive 16 holds drug reservoir 18 in contact therewith by means of housing 12. Electrode assembly 10 is connected to a source of electrical energy, usually a battery, optionally through a current controller. A second electrode assembly (ie, the counter electrode) is then placed in contact with the patient's skin at a site separate from but adjacent to the site of electrode assembly 10 to complete the circuit. Upon activation, transdermal drug or agent delivery occurs.

In accordance with this invention, electrode assembly 10 includes a uniformly or homogeneously dispersed, ion exchange material 19. As shown, ion exchange material 19 is mixed into the hydrophilic gel matrix 21 so that material 19 is uniformly distributed throughout drug reservoir 18. This feature distinguishes the present invention from prior art electrotransport systems which utilize ion exchange materials. In the prior art, the ion exchange materials are used as a discrete layer or membrane composed substantially entirely of the ion exchange material.

The electrode assembly shown in FIG. 1 also illustrates several of the terms defined above. Ion exchange material 19 is dispersed or commingled with the therapeutic agent in drug reservoir 18. The ion exchange material is dispersed throughout the drug reservoir structure. As such the drug reservoir is a "composite" structure as defined above. Regardless of the terminology, the absence of a discrete, discernable layer, coating, highly concentrated zone or region composed entirely or substantially of ion exchange material, as defined herein, is one of the primary advantages of this invention that, heretofore, has gone unrecognized.

Utilization of a dispersed ion exchange material has several advantages. First, as discussed above, the polarization effect due to Donnan exclusion is greatly reduced or eliminated. Since the ion exchange material is dispersed and does not form a discrete continuous membrane or layer, ion pathways are provided which do not exhibit such polarization effects. Second, an electrode assembly comprising dispersed ion exchange material is easier to manufacture than the same assembly having a discrete or discernable layer or membrane of such material. Generally speaking, the ion exchange material and the drug or agent to be delivered (if the ion exchange material is distributed in the drug reservoir) need only be uniformly mixed or dispersed with each other. Also, due to large surface area and the uniformity of dispersion of the ion exchange material, the ion exchange material provides a uniform distribution of ionic species and therefore a uniformly conductive composite which limits the formation of regions of low ion content (ie, a region having non-uniform concentration of ions of a particular charge which results in increased polarization). Lastly, the ion exchange material is a ready source of ionic species to capture competitive ions or facilitate reactions which generate no competitive ions. This is a distinct advantage over an electrode assembly having a defined or discrete layer or membrane where the species must diffuse to the membrane location before any particular process can occur.

It is within the scope of this invention that the ion exchange material be present in different concentrations in different portions or segments of the electrode assembly or structure. However, the ion exchange material must not be so concentrated in any segment of the structure so as to cause significant polarization due to Donnan exclusion or size selectivity considerations.

In a more preferred practice of this invention, ion exchange material may be dispersed or distributed proximate to the electroactive substance (alone or in addition to the reservoir) as described above. Distribution of the ion exchange material in the electrode has the possible advantages of (i) optimizing electrotransport drug flux when the ion exchange material is dispersed within the donor electrode assembly; (ii) providing the opportunity for early interaction between the ion exchange material and any competitive species generated by the electrochemically active substance or enhancing the facilitation of reactions which generate no competitive species and (iii) reducing skin irritation which can occur if the ion exchange material is placed in near or direct contact (eg, the material is dispersed in a skin-contact adhesive) with the patient's skin.

In contrast with Parsi U.S. Pat. No. 4,731,049, the present invention does not require the drug to be bound to an ion exchange or ligand affinity medium. In fact, in a preferred practice of this invention, ion exchange material 19 is intentionally selected so as not to bind or absorb a significant amount of the therapeutic agent. If therapeutic agents were bound to the ion exchange material, a reduction in the amount of "free" drug or deliverable species would result. Reduction in the amount of free or deliverable agent or species could reduce overall efficiency of drug delivery. The ion exchange materials described by Parsi inherently have a charge opposite the ion exchange materials described in this invention.

The above discussion has largely assumed that electrode assembly 10 was anodic. It goes without significant additional explanation that an electrode of this invention can be utilized anodically or cathodically. For example, when electrode assembly 10 is cathodic, current distribution member 26 may comprise a silver/silver chloride mesh.

Figure 2:
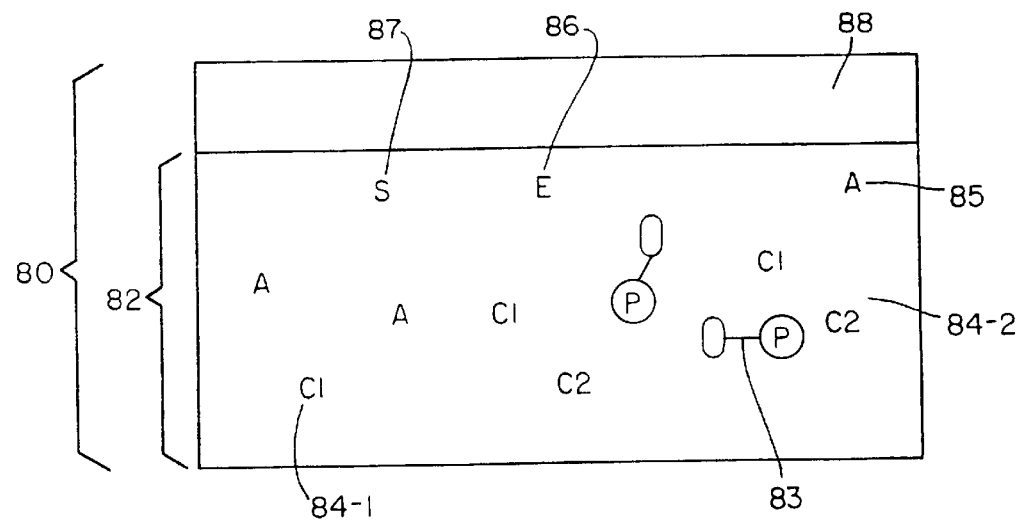
FIG. 2 is a diagrammatic illustration showing an iontophoretic electrode assembly in accordance with the present invention.

FIG. 2 is a sectional view of another active electrode assembly 80 according to the invention. (For purposes of clarity, many details of assembly 80 have been omitted.) In this embodiment, a hydrogel drug reservoir 82 (manufactured as a hydrogel or derived from hydration of substantially dry polymer) contains active agent (A) 85. Active agent 85 will generally have a cationic or anionic form. The dispersed, ion exchange material 83 has charged moieties (P) carrying the same charge as active agent 85. The mobile counter ions C1 and C2 (84-1 and 84-2) of the active agent and the ion exchange material, have an ionic charge opposite that of active agent 85. During iontophoretic operation, electrochemically generated ion E(86) interacts with one or both of the counter ions to form a substantially neutral, insoluble or immobile substance S(87).

Illustrating the above, when A is cationic, eg, protonated hydromorphone, then the ion exchange material is an organic resin with pendent cationic groups (eg, cholestyramine), the counter ions C1 and C2 are anionic (eg, chloride), the electrode 88 comprises a metal (eg, silver), E(86) is cationic (eg, silver ion) and S(87) is a substantially immobile substance (e.g, silver chloride).

When A is anionic, eg, ketoprofen, then the ion exchange material also is an organic resin with pendent anionic groups (eg, Amberlite IRP-69 sulfonated copolymer of styrene and divinyl benzene commercially available from Rohm & Haas Corporation, Philadelphia, Pa.), the counter ions C1 and C2 are cationic (eg, silver ion), electrode 88 comprises a halide salt (eg, silver chloride), E(86) is an anion (eg, chloride), and S(87) is a substantially immobile substance (eg, silver chloride).

Figure 3:
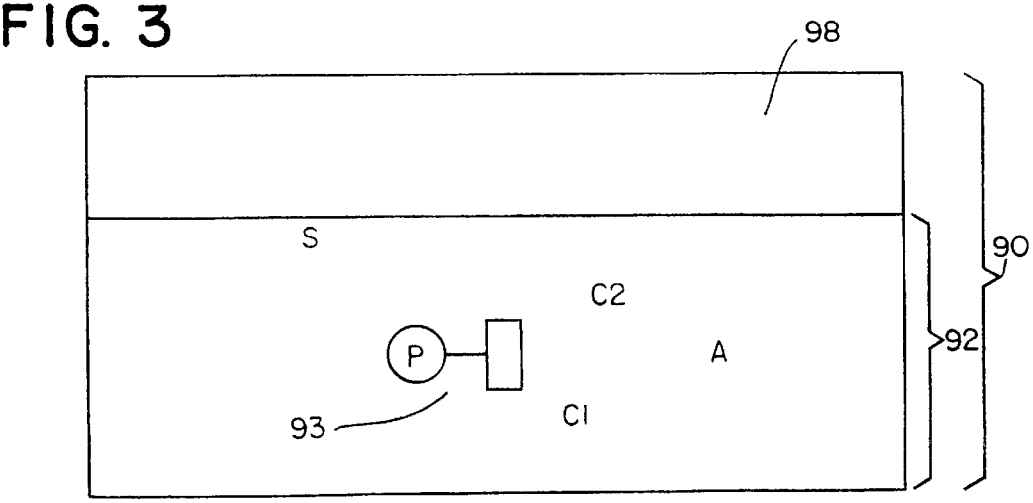
FIG. 3 is a diagrammatic illustration showing a second iontophoretic electrode assembly in accordance with this invention.

FIG. 3 is a sectional view of yet another active electrode assembly 90 according to the invention. For purposes of clarity, many details of assembly 90 have been omitted. In this embodiment, a hydrogel drug reservoir 92 contains active agent (A) which will generally have an anionic or cationic form. The dispersed, ion exchange material 93 has charged moieties (P) carrying the same charge as the active agent. The mobile counter ions (C1 and C2) of the active agent and the ion exchange material have an ionic charge opposite that of the active agent. During iontophoretic operation, the counter ion of the ion exchange material (C2), and optionally the counter ion of the active agent (C1), migrate to electrode 98 and participate in an electrochemical reaction that generates noncompetitive species (S).

More specifically, when the active agent is cationic (eg, protonated hydromorphone), then the ion exchange material component is an organic resin with pendent cationic groups (eg, cholestyramine), the counter ion C2 is anionic (eg, ferrocyanide), the active agent counter ion is anionic (eg, chloride), the electrode 98 comprises an electronically conductive material (eg, conductive carbon), and the noncompetitive species S is anionic (eg, ferricyanide).

When A is anionic (eg, ketoprofen), the ion exchange material is an organic resin with pendant anionic groups (eg, Amberlite IRP-69). The counter ion C2 is a metal cation (eg, $Cu^{2+}$), the active agent counter ion is cationic (eg, $Na^+$), the electrode 98 comprises an electronically conductive material (eg, conductive carbon), and the noncompetitive species S is metallic (eg, copper).

In each of the foregoing examples, the dispersed ion exchange material can also be amphoteric, eg, a resin with both anionic and cationic groups (eg, Bio-Rad AG 501-X8, Bio-Rad Laboratories, Richmond, Calif., USA), provided that substantially all mobile counter ions of the amphoteric polymer C2 are either ionized active agent or other ions that are oppositely charged relative to the ionized active agent. Partially neutralized salts of polyanionic or polycationic resin complexes are specific examples of amphoretic species.

Embodiments for transport of both positive and negatively charged agents, which are contained in separate elements of the electrode assembly may be utilized. In this case, both electrode assemblies will contain active agent and optionally, ion exchange material(s). Embodiments for sequential administration of two similarly charged active agents which are contained in separate electrode assemblies are also possible. In that case, the polarity of the electrode elements may be reversible. The active agent may also be a combination of substances which are to be introduced into the body. In some instances since it may be desired to introduce more than one active agent of the same charge into the body. Therefore, several active agents may be included in the same active electrode element.

The composition of the active or donor electrode assembly of the invention may include ingredients to control or alter their physical properties. Surfactants may be added to a drug reservoir to control the active agent release rate. Humectants may be added to the drug reservoir to control the evaporative loss of water. Preservatives may be added to extend the shelf life of the product. Inert fillers may be added to control the bulk density or to dilute or adjust other properties. Tackifiers may be added to enhance the adhesion of the hydrogel to the skin, electrode, or other structural components of the system. Preferably, the physical properties are adjusted so that the electrode assembly is substantially solid, that is, its consistency is such that the material does not perceptively flow.

Ingredients may also be added to the composition to color it. The coloring of the electrode element may be used as a code to identify the active agent which is admixed in the particular electrode or electrode element.

The polymers used for the polymer of the gel matrix may contain essentially any nonionic synthetic and/or naturally occurring polymeric compounds. A polar nature is preferable when the active agent is polar and/or capable of being ionic since it will enhance the likelihood of agent solubility. The gel matrix optionally will be water swellable. Synthetic polymers suitable for use in the iontophoretic electrode element are exemplified by: poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(allyl alcohol). Hydroxyl functional condensation polymers (ie, polyesters, polycarbonates, polyurethanes) are also examples of suitable polar synthetic polymers. Polar naturally occurring polymers (or derivatives thereof) suitable for use as the gel matrix are exemplified by: cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers could be used for the matrix provided that the available counterions are either drug ions or other ions that are oppositely charged relative to the active agent.

Representative ion exchange materials usable in this invention include poly(acrylic acids), poly(acrylic sulfonic acids), poly(acrylic phosphoric acids) and poly(acrylic glycolic acids), polyvinyl amines, polystyrenes, poly epichlorohydrin/tetraethylenetriamines, polymers with pendent amine groups including aromatic amine groups, optionally in combination with tackifiers, which may be included in an adhesive composition. The ion exchange materials could also be primarily inorganic in composition. Silicate and aluminate derivatives, zeolites, ceramic materials with charged surface sites and high surface area, clay materials and polyphosphazenes are possible inorganic ion exchange materials. The present disclosure is likely to suggest many organic and inorganic ion exchange materials usable in this invention to one skilled in this art.

Tackifiers are exemplified by the following materials: polybutene, terpene resins, rosin resin, paraffinic oils, glycols, glycerine, and sorbitol. Humectants which may be included are exemplified by: glycols, glycerine and sorbitol.

Drugs, therapeutic or active agents useful in the present invention include any pharmaceutical compound or chemical that is capable of being ionized or converted to a charged form or is otherwise capable of being delivered by electrotransport. Therapeutic agents, herein, are administered to a host including animals and man for the purpose of obtaining a therapeutic effect. A variety of active agents intended to be introduced into the host may be combined with the matrix. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other such species. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as buserelin, gonadorelin, napharelin and leuprolide, GHRH, GHRF, insulin, insultropin, heparin, calcitonin, octreotide, endorphin, TRH, NT-36 (chemical name: N-[[(s)-4-oxo-2-azetidinyl]carbonyl]-L-histidyl-L-prolinamide), lipercin, pituitary hormones (eg, HGH, HMG, HCG, desmopressin acetate, etc), follicle luteoids, αANF, growth factors such as growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-1, interleukin-2, mentropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSI's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Additional agents include pilocarpine nitrate, lidocaine hydrochloride, hydrocortisone derivatives, sodium salicylate, acetic acid, fluoride anion, lithium, antibiotics such as penicillin and cephalosporin and dexamethasone sodium phosphate, hydromorphone, diazepam salts, antihypertensive agents, bronchodilator agents, peptide hormone and regulatory agents and proteins.

The electrode assemblies formed using these agents are generally used as the active or donor electrodes.

The following examples are illustrative of the processes and materials used to obtain the electrode compositions of the invention. These examples should not be utilized to restrict the scope of this invention.

EXAMPLE I

This Example demonstrates the use of a metal-resin composite cathode. Two copper composite electrode compositions were prepared from copper-loaded anion exchange resins, polyisobutylene, and carbon black. In this Example, the reducible species is a mobile metal ion that is paired with a large, relatively immobile anion. Specifically, the ion pair is an immobile ionic species with a mobile copper counter ion. Upon hydration, the copper resin provides copper cations which are electrochemically reducible according to the following reaction: $Cu^{2+}+2e^-\rightarrow Cu$. The immobile ionic species does not effectively compete with an anionic drug for electrotransport delivery because the resin has a very high molecular weight. The resin is substantially immobile even under the influence of an electric field established by a DC power source connected to the cathodic electrode. Sodium diclofenac (diclofenac anions) was delivered by electrotransport from the cathode without competition from the anionic resin.

The polyisobutylene (PIB) was prepared by mixing with a cam blade mixers a 50 cm³ Brabender mixer made by Brabender Instruments, Hackensack, N.J.) a high molecular weight PIB (VISTANEX grade MM L-100 having a molecular weight of 1.2 million daltons) with a low molecular weight PIB (VISTANEX grade LM-MS having a molecular weight (MW) of about 35,000 daltons both sold by Exxon Chemical Corporation, Houston, Tex.) in about a 1:1 weight ratio. The mixing bowl was preheated to about 110° to 120° C. (230° to 250° F.) prior to addition of the high molecular weight PIB. The temperature and mixing speed (15 to 20 rpm) of the high MW PIB was continued until the viscosity was reduced to approximate that of the low MW PIB. At this point, the temperature was lowered to 90° C. (200° F.) while the low MW PIB was continuously fed into the mixer. After addition of the low MW PIB was complete, the temperature was reduced to about 80° C. (175° F.) and mixing was continued for about 20 to 30 minutes.

Copper-resins were prepared by loading copper into both a strong ion exchange resin (sulfonate end groups) and a weak ion exchange resin (carboxylate end groups). The strong ion exchange resin was AMBERLITE IRP-69, while the weak resin was AMBERLITE IRP-88, both available from Rohm & Haas, Philadelphia, Pa.

Preparation of the strong copper resin involved first dissolving about 20.2 g of copper chloride dihydrate ($CuCl_2 \cdot 2H_2O$) in about 100 g of deionized water. About 100 g of the ion exchange resin was added to the copper chloride solution over about a 10 minute period. The mixture was mechanically stirred overnight at about 25° C. After mixing ceased, the mixture was filtered to remove the liquid. The remaining resin was washed twice with about 75 mL deionized water. A second copper chloride solution (same concentration) was added to the resin and stirred overnight at about 25° C. The mixture was filtered to remove the liquid, and the remaining filtrate was washed with 75 mL volumes of deionized water until the filtrate was colorless (about five washings). The washed filtrate was rinsed with 200 mL of methanol. The rinsed filtrate was vacuum dried for about 18 hours at 0.01 kg/cm² (0.4 inches Hg) and 40° C. to produce the strong copper resin.

A similar procedure was followed in the preparation of the weak copper resin. First, about 55 g of copper chloride dihydrate ($CuCl_2 \cdot 2H_2O$) were dissolved in about 300 g of deionized water. About 100 g of the ion exchange resin was added to the copper chloride solution over about a 10 minute period. The mixture was mechanically stirred overnight at about 25° C. After mixing ceased, the liquid was decanted from the mixture. The remaining resin was washed twice with about 100 mL deionized water. A second copper chloride solution (about 55 g $CuCl_2 \cdot 2H_2O$ in about 275 mL of deionized water) was added to the resin and stirred overnight at about 25° C. Again, this mixture was decanted to remove the liquid, leaving a resin slurry. The slurry was gravity filtered and the remaining filtercake was washed with five 100 mL portions of deionized water. The washed resin was rinsed with three 100 mL volumes of methanol. The rinsed resin was air dried overnight to produce about 110 g of weak copper resin.

The composite cathodes were prepared by adding the copper-resin, PIB, and carbon black (SHAWNIGAN Acetylene Black, Chevron Chemical Company, Houston, Tex.) at about a 6.6 cm³ batch size in a Brabender mixer having an 8 cm³ volume. The compositions of the electrodes are listed in TABLE I.

TABLE I

| COMPONENT | STRONG RESIN (Vol. %) | WEAK RESIN (Vol. %) |
|---|---|---|
| PIB | 54.9 | 55.6 |
| Copper-resin | 31.4 | 30.6 |
| Carbon Black | 13.6 | 13.8 |

The batch was mixed for about 25 minutes at a temperature of about 25° to 40° C. prior to calendaring. The batch was then placed between two sheets of release liner, each having a thickness of 0.08 mm (3 mils) and fed through a pair of counter rotating calendar rolls heated to about 90° C. for 3 to 5 passes. The resulting films had a final thickness of 0.85 mm and 0.60 mm (34 and 24 mils) for the strong and weak films, respectively.

The cathodic drug reservoirs were formed by preparing a polyvinyl alcohol (PVA) hydrogel material. First sodium diclofenac (available from Sigma Corp., St. Louis, Mo.) was added to the appropriate amount of water in a mixing container and mixed until the diclofenac was completely dissolved. PVA was added to a mixing container maintained at a temperature of about 85°–95° C. and stirred for about one hour until the PVA dissolved. Hydroxypropyl methylcellulose (HPMC) was then added to the mixture and stirring was continued until the slurry appeared uniform by visual inspection. The solution was transferred to a closed cell foam mold (available from Avery Corp., Painsville, Ohio) having a 0.2 cm (1/16 inch) thickness and a 1 $cm^2$ circular cross-sectional area. The solution was allowed to cool to form a hydrogel having a disk shape. The resulting hydrogel composition was about 6% PVA, 4% HPMC, 2% sodium diclofenac and 88% water by weight.

The electrotransport delivery of diclofenac was through Poretics microporous membrane available from Poretics Corp. located at Livermore, Calif., and having a pore size of 0.09 $\mu$m, and a density of $3.6 \times 10^5$ per $cm^2$. The Poretics membrane is used as a model material to test transdermal flux. The PVA/diclofenac hydrogel disk was placed on the "donor" side of the Poretics membrane while a receptor solution comprising full strength Dulbecco's phosphate buffered saline was in contact with the "receptor" side of the Poretics membrane. A silver wire anode was placed in the receptor solution and attached to the galvanostat to complete the circuit. A constant current density of 100 $\mu A/cm^2$ was applied to the cathode in order to deliver diclofenac through the Poretics membrane. Diclofenac flux ($\mu g/cm^2$ h) was determined by measuring the diclofenac concentration of samples taken from the receptor compartment at 2 hour intervals, beginning at one hour after electrotransport was initiated. Diclofenac concentrations were measured with a high performance liquid chromatograph, commercially available from Hewlett Packard, Palo Alto, Calif. Diclofenac flux as a function of time for both the strong and weak copper-resin composite electrodes are listed in TABLE II.

TABLE II

| ELECTROTRANSPORT TIME INTERVAL (h) | Diclofenac Flux ($\mu g/cm^2 \cdot h$) WEAK RESIN | Diclofenac Flux ($\mu g/cm^2 \cdot h$) STRONG RESIN |
| --- | --- | --- |
| 0–2 | 8 | 9 |
| 2–4 | 22 | 22 |
| 4–6 | 30 | 28 |
| 6–8 | 31 | 30 |
| 8–10 | 32 | 35 |
| 10–12 | 34 | 40 |
| 12–14 | 34 | 40 |
| 14–16 | 32 | 36 |
| 16–18 | 30 | 35 |
| 18–20 | 28 | 34 |
| 20–24 | 27 | 33 |

Although the flux with the weak composite is somewhat lower, and the operating voltage (not shown) is higher than with the strong composite, the weak composite may ion exchange less during storage, depending upon the drug. Accordingly, one preferred arrangement is a strong resin composite laminated to a thin layer of a weak resin composite.

EXAMPLE II

In this example, analagous to the cathodic electrode system disclosed in Example I, an anodic electrode comprised of a polymer resin having an electrochemically oxidizable species is used to deliver a cationic drug from a polymer based drug reservoir. The electrode is comprised of a ferrocyanide form of a quaternary amine resin, for example, a styrene divinyl benzene quarternary ammonium resin in the form of a ferrocyanide salt. This type of resin can be prepared by anionic exchange of a cationic resin such as AG 1-X8, in the hydroxide form (sold by Bio-Rad Laboratories, Richmond, Calif.) whereby an appropriate amount of the hydroxide anion of the resin is exchanged for ferrocyanide anion using standard ion exchange techniques. After exchange, the resin has a backbone with a fixed positive charge and mobile ferrocyanide anions. The ion-exchange resin is placed in contact with a metallic foil current distributing member which is connected to the galvanostat. The galvanostat is set to deliver a constant current density of 100 $\mu A/cm^2$.

During application of current, ferrocyanide anions are released from the resin and are electrochemically oxidized in accordance with the following reaction: $Fe(CN)_6^{4-} \to e^- + Fe(CN)_6^{3-}$. The reaction produces no cationic species which compete with a cationic drug for delivery from an anodic electrode system. Since the oxidation potential of this reaction is lower than the oxidation potential of water, the ferrocyanide anions are oxidized in preference to water, and accordingly, generation of hydronium ions by water oxidation is substantially avoided.

The drug reservoir is made as in Example I, substituting a salt of a cationic narcotic analgesic for sodium diclofenac.

EXAMPLE III

In this Example, an electrochemically reducible cathodic electrode for electrotransport delivery of sodium ketoprofen (ie, ketoprofen anions) is prepared. The cathodic electrode contains the water soluble polymer copper 2-acrylamido-2-methylpropane sulfonate (AMPS). The mobile copper cations are electrochemically reduced during operation of the cathode in accordance with the following reaction: $Cu^{2+} + 2e^- \to Cu$. The anionic polymeric AMPS anion has a relatively high molecular weight, and hence is relatively immobile, even under the influence of an electric field established by a DC power source electrically connected to the cathodic electrode. Thus, the polymeric AMPS anions do not compete with the ketoprofen anions for electrotransport delivery.

The drug reservoir may be a PVA based hydrogel matrix similar to that described in Example I, with the substitution of sodium ketoprofen for sodium diclofenac.

A thin layer of the copper AMPS material is placed over the PVA drug reservoir. An electrically conductive carbon fiber mat is placed over the copper AMPS layer in order to provide good electrical connection to a DC power source.

EXAMPLE IV

In this Example an anodic composite intercalation electrode is used to deliver a cationic drug by electrotransport. The composite electrode is comprised of a intercalation-type material which is preferably in the form of a powder, fibers or flakes, mixed with a suitable polymer binder such as polyisobutylene. Intercalation materials for use in an anodic electrode should be oxidizable and are preferably stable in the presence of air and water when in their reduced state. Upon oxidation, the intercalation material of the composite anode will preferably incorporate anions from the surrounding medium (eg, OH$^-$ or Cl$^-$) into its structure to maintain local charge neutrality. An example of this type of intercalation material is graphite intercalated with a metal chloride, such as $FeCl_2$. Other intercalation materials will expel cations (eg, $H^+$) from their structure when oxidized.

As in Example III, the ion-conducting and/or the electron-conducting properties of this composite anode can be optionally enhanced by the addition of a hydrophilic ion-conducting material (eg, polyvinyl alcohol) or an electron-conducting material (eg, carbon black).

EXAMPLE V

In this Example, a cathodic composite intercalation electrode is used to deliver an anionic drug by electrotransport. This composite electrode is comprised of an intercalation-type material which is preferably in the form of a powder, fibers or flakes, mixed with a suitable polymeric binder such as polyisobutylene. Intercalation materials for use in a cathodic electrode should be reducible and are preferably stable in the presence of air and water when in their oxidized state. Upon reduction, the intercalation material of the composite cathode will preferably incorporate cations from the surrounding medium (eg, $Na^+$) into its structure to maintain local charge neutrality. Examples of this type of intercalation material are transition metal oxides such as tungstates, molybdates, and vanadates, or organic polymers such as polypyrroles and polyanilines. Other intercalation materials will expel anions (eg, $Cl^-$) from their structure when reduced. An example of this type of intercalation material is graphite intercalated with a metal chloride, such $FeCl_3$. In this example, the ion exchange material provides silver ions to react with the chloride ions produced.

As in Example III, the ion-conducting and/or the electron-conducting properties of this composite cathode can be optionally enhanced by the addition of a hydrophilic ion-conducting material (eg, polyvinyl alcohol) or an electron-conducting material (eg, carbon black).

EXAMPLE VI

In this Example, a source of silver ions (ie, a silver 2-acrylamido-2-methylpropane sulfonate (AMPS) polymer material) is added to the cathodic drug reservoir of a device having a metallic cathodic electrode (eg, platinum or silver). During normal operation of the device, the silver ions migrate to the metallic cathode and are reduced to silver metal. Of course, the polymeric AMPS anions remain in solution, however, because of their high molecular weight they are relatively immobile and therefore present minimal electrotransport competition.

In a preferred embodiment, the cathode is composed of silver chloride. As the silver ion is reduced and deposited on the silver chloride cathode during operation, silver ion is depleted in the vicinity of the cathode. If the migration of silver to the cathode is too slow, then the cathodic potential will increase to a level where reduction of silver chloride will occur. Chloride ion will then migrate into the hydrogel and react with the silver-AMPS to form insoluble silver chloride.

The silver AMPS material is prepared by adding silver carbonate to a 15% aqueous solution of acid AMPS gel, a non-cross linked 2-acrylamido-2-methyl propane sulfonic acid polymer available under the trade name ACCELOMER 100 from Joats, Inc. (Champlin, Minn.). The acid AMPS is converted to the silver salt by reacting with the silver carbonate, according to the following reaction: $Ag_2CO_3 + 2H\text{-}AMPS \rightarrow 2Ag\text{-}AMPS + CO_2 + H_2O$.

A polyvinyl alcohol (PVA) hydrogel is mixed with the silver AMPS and an aqueous solution of sodium diclofenac (ie, diclofenac anions) is imbibed into the PVA gel. The silver chloride cathode is placed on the diclofenac-containing PVA gel to form a cathodic electrode/drug reservoir assembly.

We claim:

1. An electrotransport device comprising:
   a donor electrode assembly,
   a counter electrode assembly,
   a source of electrical power adapted to be electrically connected to the donor electrode assembly and the counter electrode assembly, at least one of the electrode assemblies including a reservoir containing an active agent to be delivered, the reservoir adapted to be placed in active agent transmitting relation with a body surface, and the electrodes adapted to be electrically connected to the source of electrical power, and
   at least one ion exchange material distributed in a matrix, the ion exchange material providing at least one oxidizable or reducible mobile ionic specie capable of reacting with free electrons and providing at least one substantially immobile ionic specie.

2. The device of claim 1, wherein the ion exchange material is dispersed in the reservoir and the mobile ionic specie reacts with free electrons in the electrode.

3. The device of claim 1, wherein the donor electrode is anodic and the mobile ionic specie comprises chloride ions.

4. The device of claim 1, wherein the donor electrode is anodic and the mobile ionic specie includes an electrochemically oxidizable specie.

5. The device of claim 4, wherein the oxidizable specie comprises $Fe(CN)_6^{4-}$ ions.

6. The device of claim 1, wherein the donor electrode is cathodic and the mobile ionic specie includes an electrochemically reducible specie.

7. The device of claim 6, wherein the reducible specie comprises metal cations.

8. The device of claim 1, wherein the donor electrode is cathodic and the mobile ionic specie includes hydronium ions.

9. The device of claim 1, wherein an intercalation compound is located in the donor electrode assembly.

10. The device of claim 9, wherein the intercalation compound comprises $C_nFeCl_2$.

11. The device of claim 1, wherein the mobile ionic specie comprises chloride ions.

12. The device of claim 1 wherein the matrix in which the ion exchange material is dispersed is selected from at least one of the donor or counter electrode assembly, the reservoir, and an adhesive layer positioned between the reservoir and a body surface.

13. The device of claim 12 wherein the ion exchange material is distributed in at least one of the donor or counter electrode assembly in order to form a composite electrode assembly.

14. The device of claim 1, wherein the donor electrode is cathodic and the ion exchange material comprises a copper ion-loaded resin.

15. The device of claim 1 wherein the ion exchange material is selected from copper-2-acrylamido-2-methylpropane sulfonate and silver-2-acrylamido-2-methylpropane sulfonate.

16. The device of claim 1, wherein the active agent comprises a drug.

17. The device of claim 16, wherein the drug comprises a narcotic analgesic.

18. The device of claim 17, wherein the narcotic analgesic comprises fentanyl.

19. The device of claim 1, wherein the ion exchange material comprises a polymeric resin.

20. The device of claim 1, wherein the ion exchange material has a molecular weight in the range of about 1000 daltons to about 10 million daltons.

21. The device of claim 1, wherein the ion exchange material is particulate having a major dimension in the range of about 0.1 microns to about 1200 microns.

22. The device of claim 1, wherein the ion exchange material comprises an inorganic material.

23. The device of claim 1, wherein the ion exchange material is a member selected from the group consisting of poly (acrylic acids), copolymers of styrene and sulfonated divinylbenzene, and polyamines.

24. The device of claim 1, wherein the donor electrode is anodic and the ion exchange material is a ferrocyanide salt of a styrene divinyl benzene quaternary amine.

25. The device of claim 1, wherein the ion exchange material is dispersed in a hydrophilic gel in the reservoir.

26. The device of claim 1 wherein the ion exchange material does not absorb or bind a significant amount of drug.

27. A method of electrotransport agent delivery comprising the steps of:

providing an electrotransport device comprising: a donor electrode assembly, a counter electrode assembly; a source of electrical power adapted to be electrically connected to the donor electrode assembly and the counter electrode assembly, at least one of the electrode assemblies including a reservoir containing an active agent to be delivered, the reservoir adapted to be placed in active agent transmitting relation with a body surface, and the electrodes adapted to be electrically connected to the source of electrical power; and at least one ion exchange material distributed in a matrix providing at least one oxidizable or reducible mobile ionic specie capable of reacting with free electrons and providing at least one substantially immobile ionic specie; and, delivering the agent through a body surface.

* * * * *